United States Patent
Zahedi

Patent Number: 5,413,578
Date of Patent: May 9, 1995

[54] DEVICE FOR REMOVING A BONE CEMENT TUBE

[76] Inventor: Amir Zahedi, Hörsterstrasse 54, D-4400 Münster, Germany

[21] Appl. No.: 75,354

[22] Filed: Jun. 14, 1993

Related U.S. Application Data

[63] Continuation of Ser. No. 773,860, Oct. 24, 1991, abandoned.

[30] Foreign Application Priority Data

Mar. 14, 1989 [DE] Germany .......... 8903310 U
Oct. 9, 1989 [DE] Germany .......... 39 33 711.1

[51] Int. Cl.⁶ .......... A61F 5/00; A61B 17/32
[52] U.S. Cl. .......... 606/86; 606/169
[58] Field of Search .......... 606/30, 86, 87, 88, 606/167–172; 81/121.1, 124.3, 467, 472–474, 476–478

[56] References Cited

U.S. PATENT DOCUMENTS

| | | | |
|---|---|---|---|
| 3,589,363 | 6/1971 | Banko | 606/169 |
| 3,888,004 | 6/1975 | Coleman | 606/169 |
| 4,248,232 | 2/1981 | Engelbrecht | 606/169 |
| 4,609,368 | 9/1986 | Dotson | 606/169 |
| 4,846,161 | 7/1989 | Roger | 606/99 |
| 4,848,337 | 7/1989 | Shaw | 606/28 |
| 4,873,969 | 10/1989 | Huebsch | 606/92 |
| 5,059,210 | 10/1991 | Clark | 606/169 |
| 5,064,426 | 11/1991 | Huebsch | 606/92 |

FOREIGN PATENT DOCUMENTS

| | | |
|---|---|---|
| 0028712 | 5/1981 | European Pat. Off. |
| 0305627 | 3/1989 | European Pat. Off. |
| 2741107 | 3/1979 | Germany |
| 8702571 | 5/1987 | WIPO |

Primary Examiner—Michael A. Brown
Attorney, Agent, or Firm—Spencer, Frank & Schneider

[57] ABSTRACT

A device for removing a bone cement tube surrounding a prosthesis shaft from the bone cavity after removal of the endoprosthesis which comprises an ultrasonic generator with an essentially cylindrical guide section, the free end of which carries the sonotrode which emits the ultrasound, whereby the diameter of the guide section is less than the internal diameter of the bone cement tube and its length is adapted to the length of the prosthesis shaft or to the length of the bone cement tube.

19 Claims, 4 Drawing Sheets

DEVICE FOR REMOVING A BONE CEMENT TUBE

This application is a continuation of application Ser. No. 07/773,860, filed Oct. 24, 1991, now abandoned.

BACKGROUND OF THE INVENTION

The invention relates to a device for removing a cement tube remaining in a bone cavity after removing a cemented-in endoprosthesis.

Implants which are embedded in cement cannot generally remain in the bone for an unlimited length of time. If such an implant must be exchanged or removed, an essentially cylindrical bone cement tube remains in the bone after its removal, which must be totally removed for reimplantation.

The removal of the old bone cement was previously carried out by boring it out from above or by laying a bypass at an angle from underneath in order to loosen all bone cement parts using pliers or other mechanical means, in particular suction devices.

It is also known that an extractor, whose head comprises a threaded plug, be used for this purpose by being cut into the bone cement tube in order to obtain a sufficiently firm hold for the removal of the bone cement tube. This known instrument has the weighty disadvantage, that is particular with older patients, it is possible that the bone wall splits open if the radial tension, which is generated by the threaded plug, is greater than the tensile strength of the bone. There is also no guarantee, when using the extractor, that all of the bone cement at the foot end of the bone cavity will be loosened.

A combination of such an extractor with an expanding device is known from German Offenlegungsschrift (published patent application) 29 44 719, whereby the expanding device is used to grip underneath the bone cement tube, in order to ease the removal of the bone cement tube. The use of this device also leads to a substantial mechanical loading of the corticalis which surrounds the bone cement tube. The above described uncertainties, with respect to whether all of the bone cement has been removed, cannot be eliminated by the expanding device. Furthermore, it can be become necessary to enlarge the existing bone cavity in order to grip underneath the bone cement tube to obtain working space for the expanding device underneath the bone cement tube. It is also disadvantageous that an optical supervision of this manipulation and the implementation of the expanding device, for example via an x-ray picture which is transmitted to a monitor, is necessary.

SUMMARY OF THE INVENTION

An object of the present invention is to provide a device, with which it is possible that a bone cement tube be loosened and removed from the bone cavity in one piece or in a small number of fragmental pieces, without the device coming in direct contact with the bone cavity.

The above and other objects are achieved in accordance with the invention by the provision of a device for removing a cement tube remaining in a bone cavity after removal of a cemented-in endoprosthesis leaving a cavity in the cement tube, the device including: an ultrasonic generator including a guide section which can be inserted into the cavity of the cement tube, the guide section having a free end comprising a sonotrode which can emit ultrasound when guided in the cavity of the cement tube by the guide section for facilitating removal of the cement tube from the bone cavity.

According to the invention an ultrasonic generator with a guide section, which can be inserted in the bone cement tube loosens the bone cement tube. The ultrasonic generator further comprises a sonotrode, which emits the ultrasound and which is integrated in the guide section. The guide section is dimensioned such that it can be inserted in the bone cement tube, from which the prosthesis shaft has been removed, and that the sonotrode can reach the close surroundings of all of the regions of the wall, which has been created by the bone tube. Due to the sonotrode forming the free end of the guide section, all of the parts of the bone cement tube can be treated by slowly inserting or extending the guide section. The "guide section" is therefore a part which can be inserted under guidance in the bone cement tube and which therefore either partly or totally takes over the "guidance" within the bone cement tube, so that an uncomplicated handling results. The sonotrode, which emits the ultrasound, is situated in the end region of the guide section and therefore reaches the deepest section of the bone cement tube when the guide section is inserted fully. Along the insertion path or during removal all other parts of the bone cement tube can be reached.

In particular, the thus created hand-operated device comprises the mentioned guide section, which can be pushed into the bone cement cavity as far as a stop. In this manner, the ultrasonic generator can be guided in the open bone cement cavity in an axial direction after the prosthesis shaft has been removed, so that the ultrasonic generator can successively reach the close surroundings of all of the regions of the wall of the bone cement tube, which still remains in the bone.

It was found that a layer of cement, which covers a bone substance, loosens when it is ultrasonically radiated with a frequency in the region of 40 kHz and can be removed from the surface of the bone as a complete block of cement. The substance of the bone is not weakened due to this.

Such an ultrasonic generator consists of two parts: a hand-operated device and a generator which is connected to the hand-operated device via a flexible high-frequency cable. The hand-operated device also comprises, apart from a handle part which remains outside the bone, a guide section for guiding inside the bone tube, whose free end comprises a sonotrode which emits ultrasound.

The sonotrode, as the end part of the guide section, is preferably of a rounded-off shape, so that it can glide like a skid of a sledge in every possible position in the bone tube and a blocking of the gliding motion due to the tilting of the guide section is not possible.

In particular, the active surface area of the sonotrode is formed by the surface area of an essentially cylindrical section which is coaxially aligned with the longitudinal axis of the guide section. Therefore, the sonotrode and the guide section are a homogeneous body, preferably of titanium or aluminum, into which the ultrasound energy is transmitted from the part of the device situated outside the bone tube via an oscillator or something similar. The ultrasonic radiation occurs in a radial direction via the outer surface area of the sonotrode, which is integrated in the guide section. Preferably the surface area vector of the active surface area of the sonotrode is, in each case, radially in alignment with the longitudinal axis of the guide section.

In order to create a standing wave the length of the sonotrode and the frequency of the radiated ultrasound are dimensioned in a such a manner, that the length is essentially equal to a multiple of the halflength of the wavelength which occurs inside the sonotrode.

In accordance with an advantageous feature of the invention, the free end of the guide section, which comprises the sonotrode and which diminishes in size in the direction of its free end, comprises a curved section which is adapted to the prosthesis shaft, whereby the curvature is chosen so that the guide section with a constant cross-section or the guide section which continuously diminishes in size in the direction of its free end can reach the region of the bone tube furthest away from the outer access, whilst at the same time the curvature of the sonotrode part is kept as small as possible. In this manner the section of bone tube which is furthest away from the opening can be reached using a guide section which is as straight as possible. Due to the straight construction of the sonotrode section, bending oscillations, which could damage the sonotrode, can be prevented or kept small.

In order to be able to use the device in connection with as many differently formed prosthesis shafts as possible, a plurality of exchangeable guide sections comprising sonotrodes are provided.

In accordance with a further advantageous feature of the invention there is additionally provided a guide tube to take up and fix the guide section of the ultrasonic generator and which can be pushed into the inside of the cement tube. The guide tube enables the sonotrode to be displaced at a constant pace, so that all of the border surface area between the bone cement tube and the bone is swept over by the ultrasonic radiation. If the sonotrode does not emit concentrically about the tip of the guide section, but in a preferential direction which is radially aligned to the guide tube, a complicated meandering movement may be necessary. In this latter case, the sonotrode is rotated backwards and forwards by 360° minus the radial opening angle of the emitted ultrasound and is at the same time axially displaced. This form of movement is preferably to a continuous rotation and a superimposed displacement, as the hand-operated device of the ultrasonic generator does not have to be rotated together with the high-frequency cable. Such a form of movement can be easily realized with a corresponding cylindrical cam which is either attached externally to the edge of the bone cement tube and in whose meandering recess a nipple of the guide tube engages or which is directly formed in the guide tube and acts as a "guide track" for a nipple of the guide section of the ultrasonic generator. In this last embodiment the guide tube retains its relative position to the bone cement tube and the guide section is "wound out" whilst in the first case the guide section is fixed to the guide tube and both parts are wound out of the tube together.

It is also advantageous to construct the guide tube so that an endoscope, a rinsing device and/or an expanding device can be inserted through it.

The guide tube can, in accordance with a further feature of the invention, also be used in exchange with and instead of the guide section, to take up an endoscope and/or a rinsing device and/or an expanding device. Expanding devices make it possible, due to the bone cement tubes being gripped underneath, to comfortably lift out the loosened cement tube even if, after the ultrasonic treatment, a minimal additional loosening is required with hammer and chisel and the cement tube thereby possibly breaks up into a number of fragments.

In accordance with an advantageous embodiment of the invention the shape of the sonotrode is closely adapted to the shape of the removed prosthesis shaft and therefore also to that of the cavity of the cement tube. The dimensions of such a sonotrode can therefore be derived from the dimensions of the rasp used to create the bone cavity. The length of the sonotrode can be greater than that of the cement tube, whilst the diameter is at most equal to that of the cement tube and decreases in the direction of the tip. A small sabre-like curvature eases the insertion of the sonotrode into the bone cement tube. By designing the total outer surface area of the sonotrode as a surface which emits ultrasound, it is not necessary to use a guiding device, in particular a guide tube or a cam cylinder. The number of variations of this special form of the sonotrode, which is adapted to the bone cement tube, depends on the lengths of the shafts and the radii of curvature of the proximal ends of the shafts usually used.

BRIEF DESCRIPTION OF THE DRAWINGS

Further advantageous features of the invention will be described in greater detail below together with a description of the preferred embodiment of the invention as shown in the drawings.

DESCRIPTION OF THE PREFERRED EMBODIMENTS

The central configurational element of the preferred embodiment of the device according to the invention for the removal of a bone cement tube during the reimplantation of an endoprosthesis from a bone cavity is formed by an ultrasonic generator 1, which comprises a cylindrical guide section 2. The guide section 2, which is in the form of a shaft has a sonotrode 3, which emits ultrasound, positioned at its free end. At its not illustrated upper end there is a handle to guide the shaft.

Figure 1:
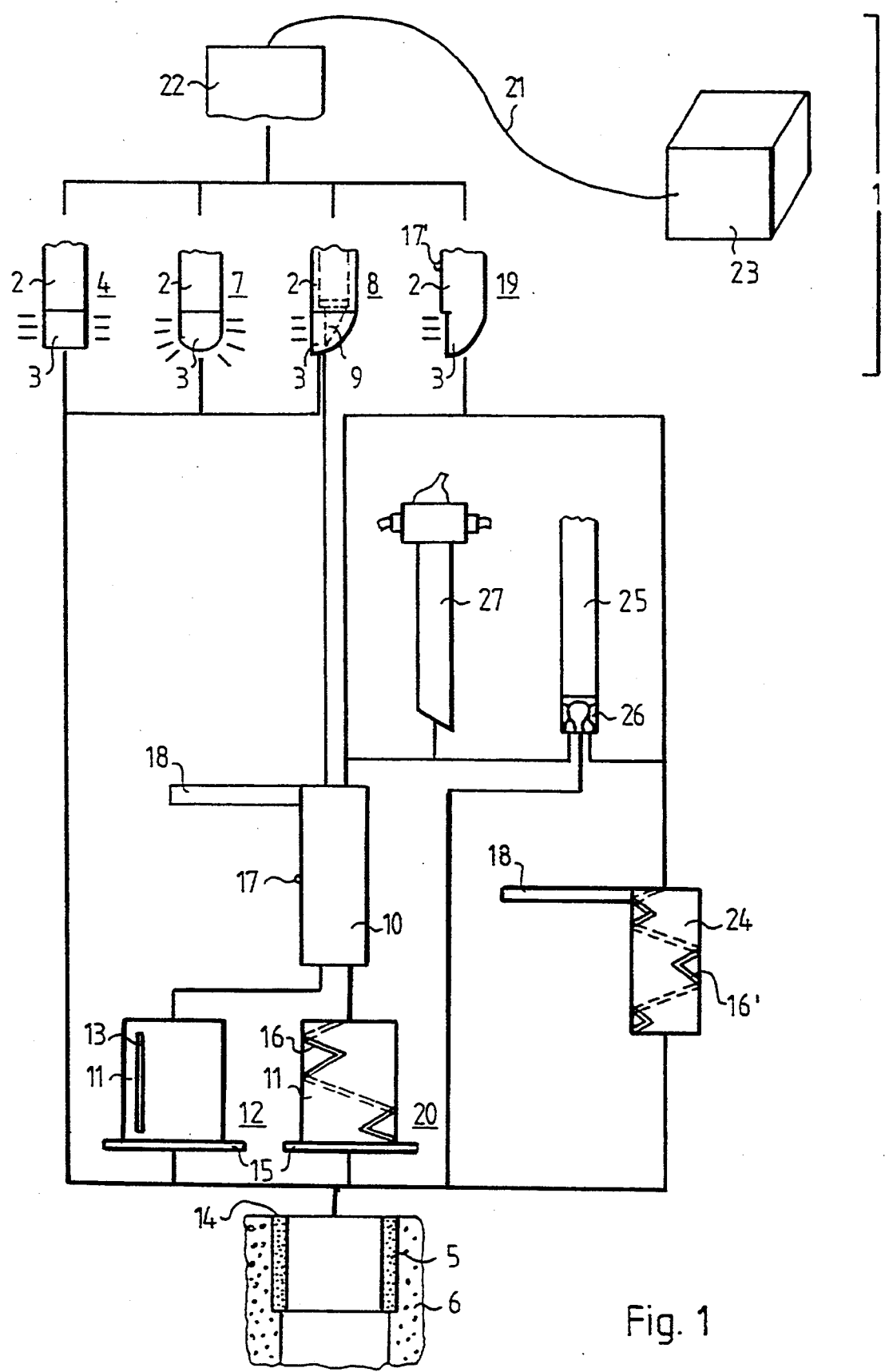
FIG. 1 is a schematic which shows the different configurational elements and their possible combinations in an overview, of the invention.

Four individual sonotrode configurations, which form more or less point sources of ultrasound, are illustrated in FIG. 1. These sonotrodes can, when configured differently, as for example those illustrated in FIG. 3, also take up more or less a large long region of the shaft-shaped guide section. The guide section makes it possible to introduce the sonotrode into the region of the cavity which is formed when the prosthesis shaft is removed.

With a first configuration 4, ultrasound is emitted from a cylindrical surface area of the sonotrode. With such a configuration 4 a uniform allround radiation of an inner surface area of a hollow cylinder can be obtained without having to rotate the sonotrode 3. A guide section 2 of an ultrasonic generator 1 with a sonotrode of the configuration 4 can be inserted directly into the bone cement tube 5 to be then taken out again whilst radiating ultrasound. In this manner, each surface element of the border surface between the bone cement tube 5 and the bone 6 can be reached by ultrasound. The same working procedure is also used with a second sonotrode configuration designated 7, which is hemispherical and is positioned at the tip of the guide section 2.

If, on the other hand, the sonotrode only radiates in the axial direction of the guide tube—as is the case with the third configuration 8, the ultrasonic waves must be deflected laterally with the help of a suitable optical element 9. It is advantageous, if the optical element 9 can be rotated manually or with a motor, so that this also results in a uniform allround radiation. Such an ultrasonic generator 1 can be inserted directly into the cement tube 5 and is manually guided by the ultrasonic generator 1.

If a controlled constrained guidance is wished, this can also be realized in a handy manner: The guide section 2, together with the sonotrode 3, is inserted in a guide tube 10, so that this, with the help of a cam cylinder, glides along a recess, whose shape enables the sonotrode to be displaced, so that it glides over all of the tube surface area. In the simplest case the cam cylinder 12 merely comprises a slit 13 in an axial direction. The cam cylinder 12 is positioned on the edge 14 of the bone cement tube 5 and therefore comprises a small collar 15.

To grip into a long recess 16 which corresponds to the curvature of the required relative displacement between the sonotrode 3 and the bone cement tube 5 with another embodiment of a cam cylinder 20 (also see FIG. 2), the guide tube 10 comprises a protruding nipple 17. This nipple 17 can preferably be sunk into a recess in the wall of the guide tube 10, due to a light loading against a small spring (not shown), which is positioned in this recess. Due to this, the engaging of the nipple 17 in the recess 16 is made easier. The guide tube 10 comprises a handle 18 to be able to guide it manually along the shape of the slit.

Figure 2:
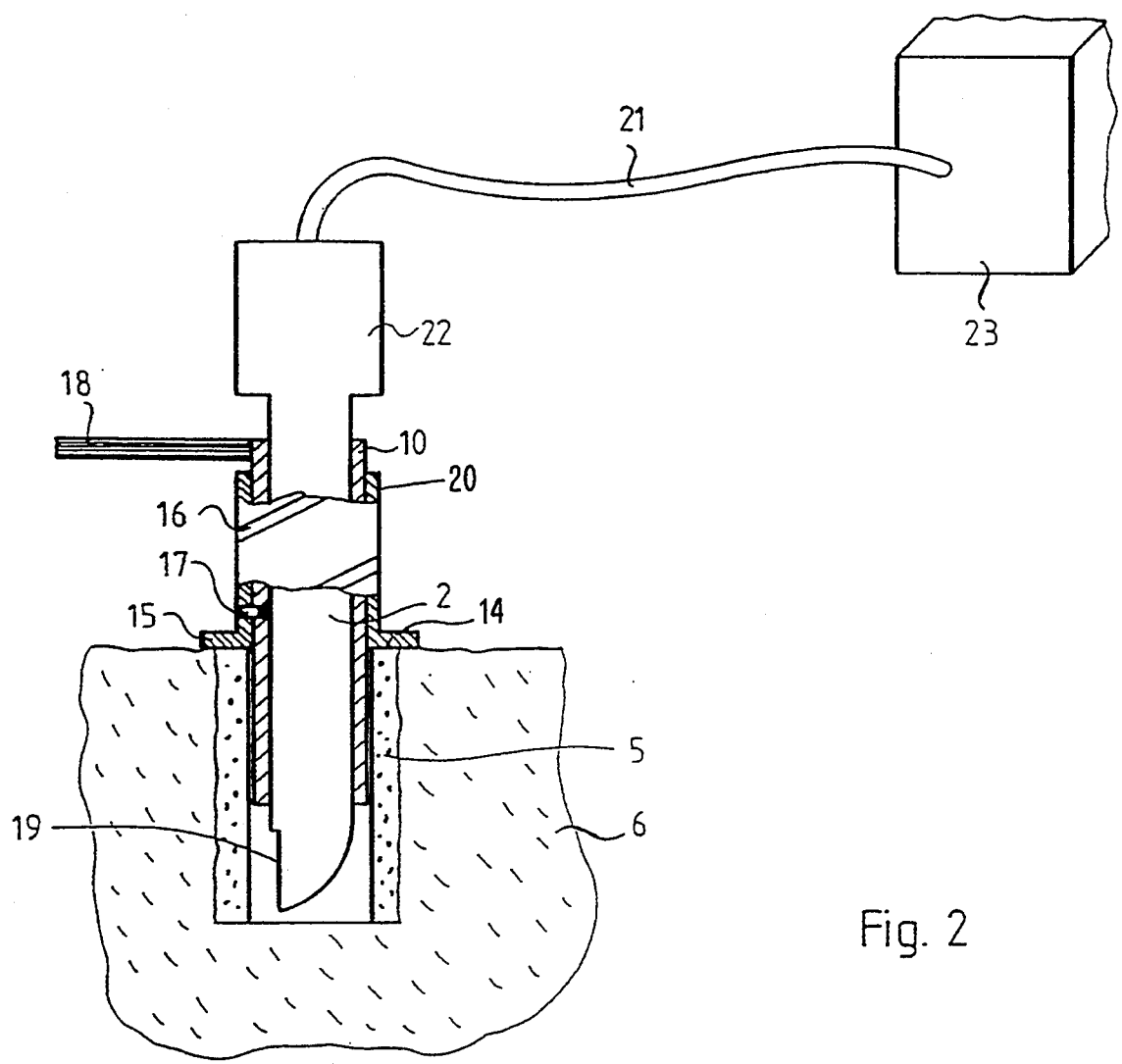
FIG. 2 is a schematic, in partial axial section which shows a further preferred embodiment of the invention with a sonotrode which emits in a preferential direction.

The recess 16 is more complicated in shape, when the sonotrode 3 does not send out ultrasound in all radial directions, but only within a certain angular region. That is the case with the fourth embodiment of sonotrode 3, which is designated 19. A guide section 2 of an ultrasonic generator 1 with such a sonotrode must be guided within the bone tube 5 so that all surface elements of the border area between the bone cement tube 5 to be removed and the surrounding bone substance 6 are radiated with the same intensity. This can be advantageously realized in that the guide section 2 is pushed into a guide tube 10 and fixed, and that this then engages in the wound recess 16 of the cam cylinder 20 and is inserted as a unit in the bone cement tube 5, whereby the collar 15 of cam cylinder 20 lies on the edge 14 of the tube 5. Such pushed together parts are illustrated in FIG. 2. The length of the guide tube 10 must be at least as long as the sum of the length of the cam cylinder 20 and the depth of the bone cement tube 5. The shape of the recess 16 can be wound like a screw or can meander. The latter is more preferable since a meandering rotation back and forth is, when compared with a screwlike complete rotation, advantageous, in that the high-frequency cable 21, which connects the hand-operated device 22 with the generator 23, does not twist.

As further shown in FIG. 1, a similar recess 16' can also be cut directly in a corresponding guide tube 24. The guide section 2 must then comprise the nipple 17'. With this variation the hand-operated device 22 of the ultrasonic generator 1 is guided. The wall of the guide tube 24, which in this case is still between the sonotrode and the bone cement tube, does not act as a hinderance for the ultrasound.

After the bone cement tube 5 has been loosened it is then taken out completely, preferably using an expanding device 25. The distal end of the expanding device 25 has wings 26 which spread apart to grip underneath the cement tube 5 or to be jammed inside the tube 5. If an exchange of the guide tube with an endoscopic device 27 is to be made possible, an above-described guide tube 10 together with a cam cylinder must be used, in order that the freedom of vision required is obtainable. The endoscope 27 is used to examine the cavity, in particular after the bone cement tube 5 has been removed and after the rinsing and vacuuming out of smaller particles.

Figure 3:
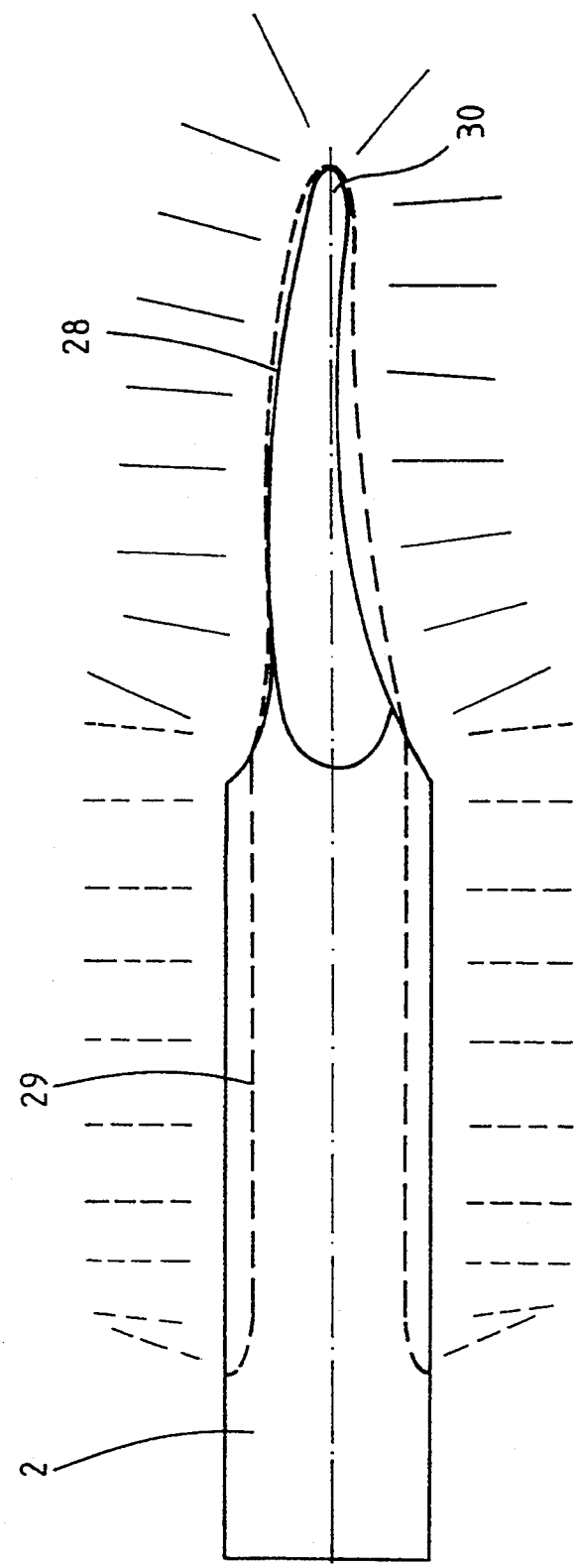
FIG. 3 is a side view of a further preferred embodiment of a sonotrode which emits in every radial direction.

FIG. 3 shows two variations 28 and 29, in full and dot-dash contour, respectively, of other embodiments to manually guide a sonotrode together with a guide section, which emit ultrasound radially from the total surface area. The length of the sonotrode corresponds at least to that of the cement tube to be loosened, and the thickness at most to that of the cement tube, whereby the thickness diminishes in the direction of the tip 30 of the sonotrode 3. The shape of the tip 30 is spherically rounded. The sonotrode 28 or 29 comprises a slight sabre-like curvature, whereby its constantly changing radius of curvature in the direction of the longitudinal axis corresponds at each point to a mean value of all of the shaft curvatures in a class of similar endoprostheses, i.e. all endoprostheses which are approximately of the same length and have similar radii of curvature at that point. A sonotrode, whose shape has been optimized in this manner allows, for example, differently shaped bone cement tubes to be removed, if these lie within a variable region of removed corresponding shaft prostheses of approximately the same length. The ultrasound emitting part of the sonotrode, which can oscillate, can extend from the free end, according to the required shape, all the way to the handle end or else not as far. When manually guided, the device according to the invention with its correspondingly dimensioned guide section glides in cement tube, which remains after the prosthesis has been removed. Even if only the tip emits ultrasound, the whole area of the cement tube is swept over when the sonotrode with attached guide section is rotated and inserted and removed, so that the bone tube can be easily removed after being loosened.

The curvature of the shaft prosthesis is somewhat problematic, as the guide section together with the sonotrode must follow this curvature. On the other hand, a curved sonotrode region leads to bending oscillations and could cause a destruction of the sonotrode.

Figure 4:
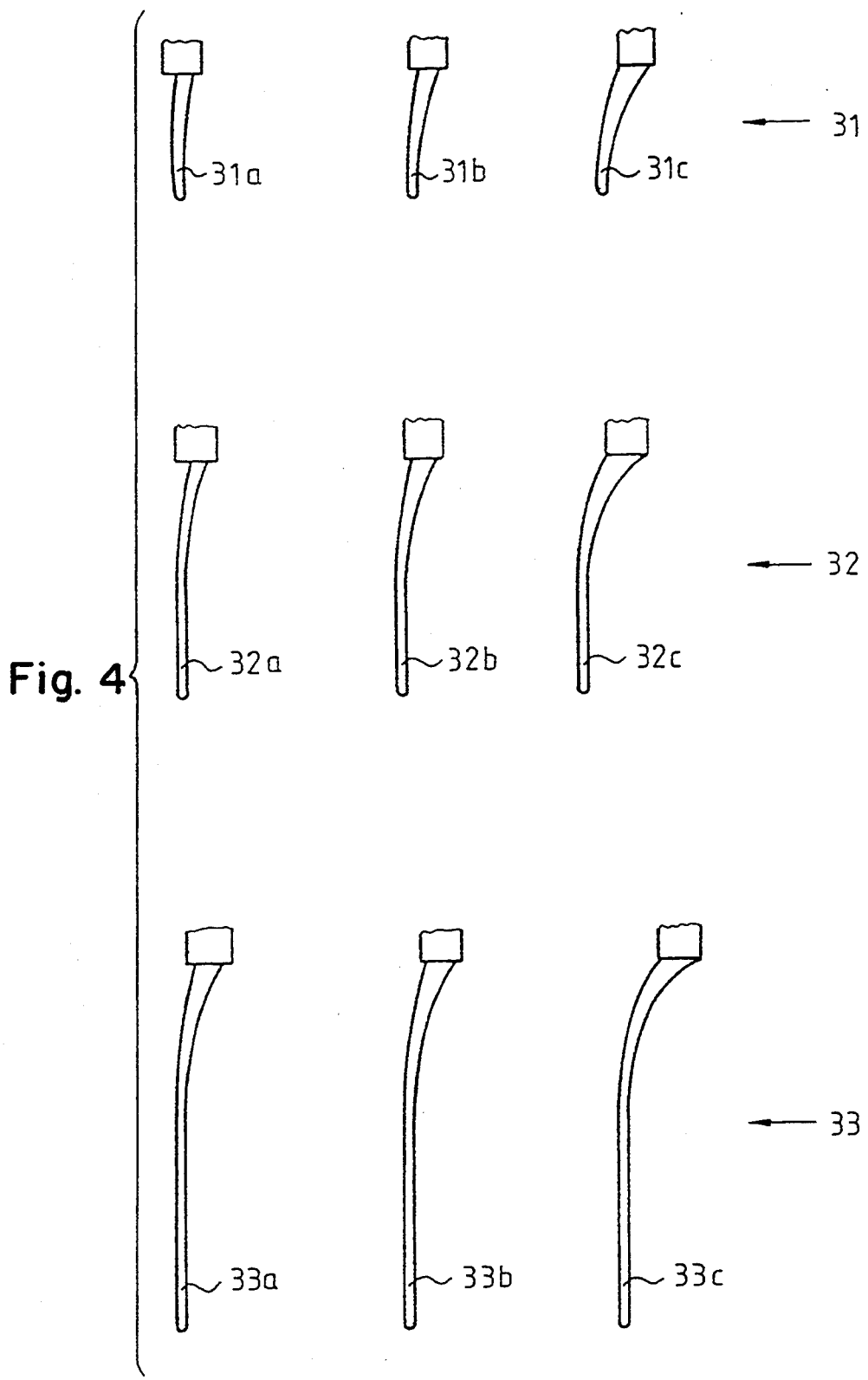
FIG. 4 an overview of differing variants of the embodiment as shown in FIG. 3.

In order to be able to remove the bone cement tube from all available prostheses, a set of guide sections was created, as illustrated in FIG. 4. In the shown overview nine variations in the shape of the sonotrode 31a, 31b, 31c, 32a, 32b, 32c, 33a, 33b and 33c are available. These can be divided into three groups 31, 32 and 33 of the same length but with stepwise varying curvatures, whereby in the illustration the length increases from the top to the bottom and the curvature increases from left to right. The length and curvature steps are usefully based on those steps used for normal bone rasps.

The shapes are chosen in such a manner, that due to the reduction of the cross-section in the direction of the free end, the free end reaches the deepest section of the bone tube. The guide section is itself kept relatively slim, so that it can be used for as many prostheses types of the length, or curvature class in question, as possible and still provide a sufficient freedom of mobility, in order to be able to move the end which comprises the sonotrode as close as possible to the inner wall of the bone tube. The active sonotrode part is to be found in the straight portion of the end section to minimize the danger of a loading of the sonotrode due to bending oscillations.

The present invention is not limited in its embodiment to the above-described preferred embodiment. Rather, a number of variations are conceivable which take advantage of the described solution even for basically different configurations.

I claim:

1. The device for removing a bone cement tube remaining in a bone cavity after removal of a cemented-in endoprosthesis, the removal of the cemented-in endoprosthesis leaving a cavity in the bone cement tube, said device comprising:
    an ultrasonic generator with a sonotrode, including a cylindrical or shaft-shaped guide section for insertion completely into the cavity of the bone cement tube for guiding the ultrasonic generator in the cavity of the bone cement tube so that the ultrasonic generator is kept in the cavity of the bone cement tube, said guide section having a free end comprising the sonotrode for emitting ultrasound when guided in the cavity of the bone cement tube by said guide section thereby facilitating removal of the bone cement tube from the bone cavity.

2. The device according to claim 1, wherein said sonotrode has a rounded shape.

3. The device according to claim 2, wherein said sonotrode has an active surface comprising a surface area of an essentially cylindrical section which is coaxial to a longitudinal axis of said guide section.

4. The device according to claim 2, wherein said sonotrode has a an active area that includes a planar surface vector radially aligned to a longitudinal axis of said guide section.

5. The device according to claim 2, wherein said sonotrode comprises one of an aluminum and titanium alloy.

6. The device according to claim 2, wherein said sonotrode has a length and an ultrasonic frequency which are dimensioned so that the length of said sonotrode is essentially equal to a multiple of half of a wavelength which occurs in said sonotrode.

7. The device according to claim 2, wherein said guide section has an outer diameter, and said device further comprises a guide tube having an internal diameter corresponding to the outer diameter of said guide section and disposed coaxially with said guide section.

8. The device according to claim 7, wherein said guide tube is fixed to said guide section and has a guide element on its periphery, and said device further comprises a cup cam cylinder having a recess into which said guide element engages when said guide tube together with said guide section is inserted into said cup cam cylinder, said recess having a shape which forces a curved motion of the sonotrode relative to said cud cam cylinder for causing said sonotrode to sweep a closed region of the bone cement tube into which said guide section and said guide tube are inserted.

9. The device according to claim 8, wherein said cup cam cylinder has an end shaped for sitting on an end region of the bone cement tube and in whose recess there engages a nipple of the guide tube.

10. The device according to claim 9, wherein said guide tube is constructed for passage of at least one of an endoscope, a flushing device and an expansion instrument therethrough.

11. The device according to claim 1, wherein said guide section has a guide element on its periphery and further comprising a cup cam cylinder having a recess into which said guide element engages when said guide section is inserted into said cup cam cylinder, said recess having a shape which forces a curved motion of the sonotrode relative to said cup cam cylinder for causing said sonotrode to sweep a closed region of the bone cement tube into which said guide section is inserted.

12. The device according to claim 11, wherein said cup cam cylinder has an end shaped for sitting on an end region of the bone cement tube.

13. The device according to claim 1, wherein said guide section diminishes constantly in cross section in the direction of said free end and includes a portion having a curvature which corresponds to a curved shape of a shaft of the removed endoprosthesis, whereby the curvature of the portion of said guide section is chosen so that said guide section reaches an area of the bone cement tube cavity farthest away from an outer entrance of the bone cement tube with the least possible curvature.

14. The device according to claim 13, wherein said guide section comprises a plurality of guide sections having at least one of differing lengths and curvatures said guide sections comprising exchangeable sonotrodes.

15. The device according to claim 1, wherein said guide section diminishes constantly in cross section in the direction of said free end and includes a portion having a curvature which corresponds to a curved shape of a shaft of the removed endoprosthesis, whereby the free end comprising said sonotrode is stretched out.

16. The device according to claim 15, wherein said guide section comprises a plurality of guide sections having at least one of differing lengths and curvatures said guide sections comprising exchangeable sonotrodes.

17. A method for removing a bone cement tube remaining in a bone cavity after removal of a cemented-in endoprosthesis, the removal of the cemented-in endoprosthesis leaving a cavity in the bone cement tube, said method comprising:
    inserting an ultrasonic generator including a cylindrical or shaft-shaped guide section having a free end comprising a sonotrode into the cavity of the bone cement tube, the guide section keeping the ultrasonic generator in the cavity of the bone cement tube; and
    emitting ultrasound from the sonotrode while the sonotrode is guided in the cavity of the bone cement tube for loosening the connection between the bone cement tube and the surrounding bone to facilitate removal of the bone tube from the bone cavity.

18. The method according to claim 17, including fixing a guide tube to the exterior of the guide section; providing a guide element on the periphery of the additional guide tube; providing a cam cylinder with a recess and locating the cam cylinder adjacent an end of the bone cement tube; and inserting the guide tube together with the guide section into the cam cylinder so that the guide element engages the recess and forces the sonotrode to follow a curved motion relative to the cam cylinder for causing the sonotrode to sweep a closed region of the bone cement tube into which the guide section and the guide tube are inserted.

19. The method according to claim 17, and further including providing the guide section with a guide element on its periphery; providing a cam cylinder having a recess and locating the cam cylinder adjacent an end of the bone cement tube; inserting the guide element into the cam cylinder so that the guide element engages the recess and forces the guide section to follow a curved motion relative to the cam cylinder for causing the sonotrode to sweep a closed region of the bone cement tube into which the guide section is inserted.

* * * * *